US006815591B1

(12) United States Patent
Hignight et al.

(10) Patent No.: US 6,815,591 B1
(45) Date of Patent: Nov. 9, 2004

(54) ENHANCING ENDOPHYTE IN GRASS

(75) Inventors: Kenneth W. Hignight, Jefferson, OR (US); Debra L. Rush, Albany, OR (US)

(73) Assignee: Advanta Seeds B.V., Kapelie (NL)

( * ) Notice: Subject to any disclaimer, the term of this patent is extended or adjusted under 35 U.S.C. 154(b) by 0 days.

(21) Appl. No.: 09/958,506

(22) PCT Filed: Apr. 14, 2000

(86) PCT No.: PCT/US00/10030

§ 371 (c)(1),
(2), (4) Date: Oct. 9, 2001

(87) PCT Pub. No.: WO00/62600

PCT Pub. Date: Oct. 26, 2000

Related U.S. Application Data
(60) Provisional application No. 60/129,673, filed on Apr. 16, 1999.

(51) Int. Cl.$^7$ ................................................ A01H 5/00

(52) U.S. Cl. ....................... 800/320; 800/298; 800/295; 424/93.5; 435/243; 435/254.1; 435/911

(58) Field of Search ................................. 800/320, 260, 800/298, 295; 426/636; 435/254.1, 243, 254, 911; 424/93.5

(56) References Cited

U.S. PATENT DOCUMENTS

| | | | |
|---|---|---|---|
| 4,847,243 | A | 7/1989 | Wallace |
| 4,940,834 | A | 7/1990 | Hurley et al. |
| 5,372,818 | A | 12/1994 | Cross et al. |
| 5,723,720 | A | 3/1998 | Brede et al. |
| 6,072,107 | A | 6/2000 | Latch et al. |
| 6,111,170 | A | 8/2000 | Latch et al. |
| 6,180,855 | B1 | 1/2001 | Hiruma et al. |

FOREIGN PATENT DOCUMENTS

| | | |
|---|---|---|
| AU | 9173853 | 7/1993 |
| EP | 753259 | 1/1997 |
| EP | 832557 | 9/1997 |
| JP | 05317092 | 3/1993 |
| JP | 07274723 | 10/1995 |
| JP | 09037667 | 10/1997 |
| WO | WO 96/39807 | 12/1996 |

OTHER PUBLICATIONS

Christensen, M. J., Variation in the ability of Acremonium endophytes of *Lolium perenne, Festuca arundianacea* and *F. pratensis* to form compatible association in the three grasses, 1995. Mycological Research 99: 466–470.*
Schardl et al, Protective grass endophytes: Where are they from and where are they going? 1997. Plant Disease 81 (5): pp. 430–438.*
C.W. Bacon et al. Modification and uses of Endophyte–enhanced turfgrasses: a role for Molecular Technology. Crop. Sci. vol. 37 No. 5 (1997), 1415–1425.
G.C.M. Latch, An overview of Neotyphodium–grass interactions. Neotyphodium/Grass Interactions, Plenum Press, (1997); 1–11.
C.P. West. Physiology and drought tolerance of Endophyte–infected grasses. CRC Press Inc. (1994); Chapter 7; 87–99.
D.D. Rowan and G.M. Latch. Utilization of Endophyte–infected Perennial Ryegrasses for increased insect resistance. CRC Press Inc. (1994), Chapter 12, 169–183.
S.G. Yates et al. Analysis of Loline Alkaloids in Endophyte–infected tall fescue by capillary gas chromatography. J. Agric. Food Chem (1990), 36, 162–185.
A.M. Craig et al. Improved extraction and HPLC methods for ergovaline from plant material and rumen fluid. J. Vet Diagn Invest (1994) 6: 348–352.
M.R. Siegel et al. Fungal endophyte–infected grasses: Alkaloid accumulation and aphid response. Chemical Ecology, vol. 16, No. 12, (1990), 3301–3315.
M.J. Christensen et al. Taxonomy of Acremonium endophytes of tall fescue (*Festuca arundinacea*), meadow fescue (*F. pratensis*) and perennial ryegrass (*Lolium perenne*), Mycol, Res 97 (9), (1993), 1083–1092.
M.P. Rolston."Use of Endophyte in Plant Breeding and the Commercial Release of New Endophyte–Grass Associations". Proc. of the second Int'l Symposium on Acremonium/Grass Interactions: Plenary Papers (pp. 171–174).
A. Leuchtmann. "Isozyme Relationships of Acremonium Endophytes from Twelve Festuca Species". Mycol. Research Abstract, (1994) vol. 98, pp. 25–33.
M.J. Christensen. "Variation in the Ability of Acremonium Endophytes of Lolium Perene, *Festuca arundinacea* and *F. pratensis* to Form Compatible Associations in the Three Grasses", Mycol. Research Abstract, (1995) vol. 99, No. 4, pp. 466–470.

(List continued on next page.)

*Primary Examiner*—Bruce R. Campell
*Assistant Examiner*—June Hwu
(74) *Attorney, Agent, or Firm*—Dana S Rewoldt

(57) ABSTRACT

The present invention relates to plants that are stably infected with an endophyte fungus. The purpose in providing to plants unique fungal endophytes is to import desired traits. These traits include insect resistance and drought tolerance and improved persistence to the plants. The plants specifically grass without inoculation with the endophyte would not evidence these traits as strongly. Endophyte inoculated grass can be used as turfgrass or foraging material depending on the grass type selected. In the present invention an endophyte that has a native host of meadow fescue was discovered. This endophyte did not provide animal toxicity's. This endophyte was transferred to a non-native host, *Lolium perenne* L. The transfer of *Neotyphodium siegelii* to *Lolium perenne* L. as a host was unique. The endophyte when in the non-native host evidenced stable inheritance and lacked the herbivore toxic effect. Inoculation of the endophyte into *Lolium perenne* produces a non-toxic grass product for mammals while deterring insects and improving drought tolerance. The grass product can be utilized for grazing animals.

17 Claims, No Drawings

OTHER PUBLICATIONS

M. Justus, et al. "Levels and Tissue Distribution of Loline Alkoloids in Endophyte–Infected *Festuca pratensis*". Phytochemistry, (1997) vol. 44, No. 1, pp. 51–57.

Z. An, et al. "Relationships Among Non–Acremonium sp. Fungal Endophytes in Five Grass Species". Applied and Environmental Microbiology (May 1993) pp. 1540–1548, vol. 59, No. 5.

G.C.M. Latch. "Influence of Acremonium Endophytes on Perennial Grass". New Zealand Journal of Agricultural Research (1994), vol. 37, pp. 311–318.

K.W. Hignight. "A Clearing Technique for Detecting the Fungal Endophyte Acremonium sp. in Grasses" Biotechnic & Histochemistry, vol. 68, No. 2, pp. 87–90.

* cited by examiner

ENHANCING ENDOPHYTE IN GRASS

PRIORITY CLAIM FOR THE U.S. DESIGNATION ONLY

This application claims priority benefit of U.S. provisional Appln. No. 60/129,673, filed Apr. 16, 1999, and international Appln. No. . PCT/US00/00086, filed Jan. 5, 2000 and designating the U.S.

BACKGROUND

1. Field of the Invention

The present invention relates to plants that are stably infected with an endophyte fungus. The purpose in stably infecting plants with unique fungal endophyte is to import desired traits. These traits include no adverse effect on herbivore, insect resistance, drought tolerance and improved persistence in the plants. The plants, specifically grass without inoculation, with an endophyte would not evidence these traits as strongly as inoculated grasses. Endoophyte inoculated grasses can be used as turfgrass or foraging material depending on the grass type selected.

2. Description of Related Art

Grasses whether turf or forage, grow in various environmental conditions. Grass is subjected to such environmental stress such as drought, acid, basic and saline/sodic soil types, excessive water, frost and freezing temperatures, chemical applications and wide temperature changes. Additionally, grass is subjected to wounding stress. Grazing animals produce wounds as do insects, fungi, and nematodes and other predators. Considering these challenges it is surprising that grass is found world-wide, however, grass thrives world-wide because grass is adaptable. One of the adaptations a number of grasses have made is the positive association with fungal endophytes. Grasses exploit endophytes as a defence mechanism against a number of the adverse challenges listed above. Endophytes exploit grasses by obtaining nutrients from the grass host. Endophytes infecting the grass host provide a biological control system to the grass that reduces the damage of insect pests and diseases. When compared to the same uninfected grasses, improved drought tolerance and nitrogen use has been shown by endophyte infected grasses.

*Neotyphodium* and *Epichloe* endophytes occur in a number of different host grasses. These hosts include tall fescue, meadow fescue, fine fescues and ryegrasses. Many of the Neothyphodium endophytes produce alkaloids that are detrimental to herbivores. Cattle grazing on a tall fescue host infected with *Neotyphodium coenophialum* may suffer from fescue foot, fat necrosis or fescue toxicosis. The endophyte *N. lolii* in perennial ryegrass causes a neuromuscular disorder know as staggers in sheep, goats, horses, buffalo and deer. The endophyte that infects *Achnatherium inebrians* (drunken horse grass) causes horses and sheep to be intoxicated for up to 24 hours. The endophyte in sleepy grass (*Stipe robusta*) is held responsible for making animals suffer narcosis.

On the other hand, these same types of endophytes, provide beneficial effects to the grasses hosting them. For example, timothy (*Phleum pratense*) plants infected with the *E. typhina* endophyte resists leafspot fungus (*Cladosporium pheli*), tall fescue hosting *N. Coenophialum* is more resistant to *Rhizoctonia zeae*, and endophyte infected fine fescues show enhanced resistance to dollar spot (*Sclerotinia homoeocarpa*). In addition to increased disease resistance, benefits from endophyte infection include the host plants ability to withstand drought stress and resistance to insects. Many tall fescue infected by *N. coenophialum* show drought tolerance, increased herbage production and increased plant tillering. Decreased insect feeding is apparent in many turfgrass cultivars having a high percentage of *Neotyphodium* endophytes. Endophyte infected tall fescue resists feeding by billbugs, sod webworms, fall armyworms. Infected fine fescue resist feeding by hairy chinch bugs; and infected perennial ryegrasses resist feeding by: sod webworm, chinch bug, Argentine stem weevil, and billbugs.

Recently the relationship between symbiotic fungal endophytes and host grasses such as tall fescue (*Festucae arundinacea* Schreb.) perennial ryegrass (*Lolium perenne* L) and the fine fescues (*Festuca* spp.) has been the subject of research. Although this symbiotic relationship is beneficial to the grass and the endophyte, it is adverse to herbivores that are devouring the grass. Endophytes that associate naturally with perennial ryegrass, tall fescue and annual ryegrasses (*Temulentumas multiflorum*) as a host are known for producing toxicity in livestock.

The role between the health of a grazing animal and endophyte infection in the pasture grass was first noted by Bacon et al. Appl. Environ. Microbiol. 34 pg. 576–581 (1977). The outgrowth of this type of research led to the observation of the interactions between endophytes and grasses. In 1983 the U.S. Pat. No. 4,940,834 was filed on selected endophytes.

This patent relates specifically to the selection of the *Lolium* endophyte fungus (*Epichloe typhina, Acremonium coenophialum*). This patent taught the discovery that endophytes confer insect resistance and certain other performance enhancing traits on the natural host. The patent taught development of perennial ryegrass having a native endophyte capable of enhancing the performance characteristics of the host, crossing the ryegrass with paternal pollen and producing progeny containing the endophyte from the cross. Paired hybridisation or recurrent selection or multiple hybridisation was used to propagate the progeny plants. This patent did not provide a method of avoiding the herbivore toxicity problem associated with *Lolium perenne* L. hosted endophytes.

The PCT international application PCT US96/0927 published in December of 1996 described the introduction of endophytes into Bentgrass. Bentgrass does not, in its native state, support endophytes. The application teaches that by crossing uncultivated grass such as wild Bentgrasses that are native hosts to endophytes with native Bentgrasses (which are not native hosts) the cultivated Bentgrasses can be stably infected with the endophyte. In another aspect of the invention the inoculation of the plant tissue of a Bentgrass is taught.

There is an U.S. Pat. No. 5,723,720 issued Mar. 3, 1998 entitled, "Process for the development of endophyte-infected plants". This patent describes infection of Bentgrasses and Kentucky grasses with endophytes.

Meadow fescue plants that were infected with N. uncinatum were shown to have the beneficial effect of better survival to certain diseases. The infected meadow fescue seedlings survived disease attack by *Drechsiera sorokiniana* and Rhizoctonia better than the non-infected seedlings. However, poorer survival was shown when the infected meadow fescue seedlings were infected by *Fusarium culmorum* than when the endophyte free seedlings were infected. This was reported in 1994 by Schmidt, D. Influence Of Endophytes Of *Festuca Pratensis* On Damping Off Diseases Of Seedlings. P. 267–273. In K. Krohn, etal. (etal.

(ed.) Intl. Conf. On Harmful and Beneficial Micro. In Grassla. Pastures and Turf. Paderborn, Germany. The issue of herbivore toxicity was not the focus of this paper.

DESCRIPTION OF THE INVENTION

Though endophytes appear to be useful for providing non-forage grass with additional stress tolerances, most commercial forage grasses cannot benefit from these increased stress tolerances, since forage grasses usually do not contain endophytes because of herbivore toxicity.

Herbivore toxic alkaloids are present in native perennial ryegrasses, which contain endophytes. However, natural perennial ryegrasses, which are not, infected with endophytes lack the performance enhancing characteristics bestowed by the endophyte on its host. There remains a need to provide Lolium perenne L. with certain performance enhancing characteristics such as persistence, drought tolerance, insect feeding resistance and disease resistance while maintaining its suitability as a forage grass and/or a turf grass.

To solve this problem a beneficial endophyte that could host on Lolium perenne L (is herein defined to include L. temulentuams multiflorum wherein the term perennial ryegrass is herein defined to exclude L. temulentuam) and is not carrying alkaloids that are toxic to herbivores had to be discovered. Most endophytes whose native host is Lolium perenne cause toxicity in herbivores thus rendering such endophytes unsuitable for solving the problem. In the present invention an endophyte that has a native host of meadow fescue was discovered. This endophyte which was misclassified as Neotyphodium uncinatum and given the P.I number 237707 does not provide compounds known to cause animal toxicities. This endophyte may be a new class of endophyte not previously discovered as it does not have the expected toxicites of Neotyphodium uncinatum. In fact, this endophyte appears to be a new species. The endophyte of the present invention is not believed to be a Neotyphodium uncinatum nor Eepichloe festucae. This endophyte may possibly be a hybrid between festucae and bromicola. Regardless of the classification this endophyte is available from the American Type Culture Collection, (ATCC), at 10801 University Blvd., Manassas, Va. 20110 deposit no. 74483 deposited on Jan. 22, 1999 For purposes of this application the endophyte of the present invention will be referred to as Neotyphodium siegelii. Neotyphodium siegelii according to this invention shall contain the characteristics of the P.I. US plant introduction collection maintained in Pullman Wash. USA, Accession # P.I: 237707. This endophyte was transferred to a non-native host, Lolium perenne L. The transfer of Neotyphodium siegelii to Lolium perenne L. as a host is unique. The endophyte when in the non-native host evidenced stable inheritance and lacked the herbivore toxic effect, due to its failure to produce toxic alkaloids in the infected host.

Inoculation of the endophyte into Lolium perenne produced a non-toxic grass product for mammals while deterring insects and improving drought tolerance. This grass product contains the endophyte of the present invention and still this product can be utilised for grazing animals.

The endophyte according to the present invention provides the following beneficial traits to the non-native host plant. If the non-native host plant is Lolium perenne then the following enhanced performance characteristics are evidenced, resistance to insect feeding, disease and water stress tolerance. Although this endophyte may show some slight increased selective insect feeding or increased sensitivity to certain diseases, overall this endophyte provides to the infected grass beneficial effects. The infected Lolium perenne evidences less insect feeding than non-infected Lolium perenne according to the present invention. The following insects decrease feeding on endophyte infected grasses: Argentine stem weevil, Sod webworm, Chinch bug, Billbug, Aphids.

The following diseases may be less likely to infect the present invention or are tolerated better by the grass when the invention is present: Drechslera spp., Rhizoctonia cerealis.

The following conditions of water stress may be more tolerated by plants infected with the endophyte according to the present invention: summer water stress and closer clipping of the grass during summer water stress.

The following toxic alkaloids are not produced by the endophyte, Neotyphodium siegelii when hosted in Lolium perenne: Lolitrem B, Ergotamine, Ergovaline and Peramine. This new endophyte does produce the alkaloid loline. Loline has not been shown to be toxic to livestock but is thought to deter insect feeding.

The endophyte of the present invention can be used to infect at least the following grass species: Lolium perenne, Lolium multiflorum, Festuca pratensis, Tall fescue, etc. The following commercial cultivars are particularly useful when infected with the endophyte of the present invention: Aubisque, Rosalin, Bastion. There are many different cultivars that would be useful. Cultivars would benefit regardless of whether the cultivar is employed as a forage grass or as an amenity or turfgrass.

The specific endophyte Neotyphodium siegelii of the present invention was found in US plant introduction collection maintained in Pullman Wash. USA, Accession # P.I. 237707. This source or other sources of this endophyte can be transferred to other non-native hosts beyond Lolium perenne. Once the infection of the non-native host is complete simple tests for enhanced performance characteristics can be performed. These test methods are known to those skilled in that art. The known method for testing for toxic alkaloids is shown in the examples. If the non-native host can be infected with the present invention and locks the toxic alkaloids and shows at least one performance enhancement then it can be used within the scope of this invention.

The specific technique for endophyte culture and inoculation shown in the examples is not difficult nor is it the only method that can be employed in the scope of the present invention. It is a technique used widely by many laboratories.

EXAMPLES

Example 1

Technique for Culture and Inoculation of Endophyte

1. Mature tillers were collected from a known endophyte source. A leaf peel stain was used to confirm the presence of the endophyte.

2. Tillers were cut to 2–3 cm long.

3. Sterilise sheath 3 min. in 100% (chloride bleach) Clorox® with constant stirring.

4. The sheaths were then rinsed 3 times with sterile distilled water.

5. In the sterile distilled water 3 cc triple antibiotic were added to the sheaths stirring was continued.

6. A few sheaths were removed at a time. 2–3 mm was cut off each end and then cut longitudinally. We discarded the outermost sheath.

7. The inner sheath was placed on Potato Dextrose Agar (PDA) available from Difco Laboratories with antibiotic. The antibiotic contained Oxytetracycline, Penicillin & Benzathine, Penicillin & Procaine. The interior side of sheath should be placed in contact with agar.

8. The material was incubated in the dark for 2 weeks at 20C.

9. After transferring small amounts of mycelium to PDA with cellulose membrane. We incubated in the dark at 20C for 3 weeks.

10. Then we surface the sterilised seed.

a. 50% sulphuric acid for 8 minutes, triple rinsed with sterile distilled water.
   b. 2.5% sodium hyperchlorite for 7 minutes, triple rinsed with sterile distilled water.
   c. Added to sterile distilled water 3 cc of triple antibiotic (listed above).

11. Then placed 3–4 seeds per plate on 2% Water Agar available from Difco Laboratories. We followed the instructions on package.

12. Placed in the dark for 7–14 days at 22C. Checked for emergence of meristem.

13. Placed a small amount of mycelium from endophyte into meristem with a #1 insect pin.

14. Placed inoculated seedling into the dark for 5–7 days.

15. Placed seedlings into growth chamber at 20C for 5–7 days.

16. Transferred seedlings to soil.

17. Presence of endophyte was determined by a leaf sheath test after multiple tillers had been established.

We took the seedlings that retained the endophyte and allowed them to reach sexual maturity. These plants were interpollinated end only the seed from the material plants were harvested. Seeds from Rosalin infected with endophyte (Rosalin E+) and from the target host should be planted. The Rosalin E+ seedlings should be allowed to grow for several months and then checked for the presence of endophyte. Seedlings, which do not show endophyte, should be removed. A variety of breeding methods can then be utilised to introduce this endophyte into other plants. Such breeding methods are: topcross, backcross, paired matings (harvesting seeds only the Rosalin E+ plants). A variety of the breeding methods listed in Walter, R. Fehr, Principles of Cultivar Development Vol I Chap 7 and 12 ISU MCGraw-Hill; 2) Briggs, Knowles, Introduction to Plant breeding University of Calif. Davis Calif.) can also be employed. The resultant cultivars were given a designation.

Grasses infected with endophytes which are not within the scope of the invention produce two classes of alkaloids that have been associated with toxicity and thus production losses in herbivores. These classes of alkaloids are the ergot type and the lolitrem type. The ergot type for example ergovaline and ergotanine, and the lolitrem type, lolitrem, paxilline, lolitrol, are present in grasses only when endophytes are present. Thus the present invention was tested for these individual toxic alkaloids. The loline alkaloids, N-acetylloline, N formylloline are considered to be beneficial alkaloids since they have not been shown to cause deleterious effects to herbivores. This loline alkaloid has been shown to be important for insect resistance. This alkaloid is not normally found in perennial ryegrass except in low quantities and in association with toxic classes of alkaloids. The endophyte of the present invention appears to carry some of the loline alkaloids.

Example 2

Testing Loline

Loline alkaloid analysis was carried out essentially as described by Yates and co-workers (J. Agric. Food Chem. 1990, 38:182–185). using a Supelco SPB™-1 capillary column (15 mm×0.53 mm×0.5 cum) and a Hewlett Packard 5890 Series II Plus gas chromatograph. Sample (50 mg dried ground tissue) was wetted with 100 ul saturated sodium bicarbonate and extracted for 0.5 hr with 1 ml of an extraction solution consisting of 5% ethanol in methylene chloride with phenylmorpholine (25 mg/L) as an internal standard.

The listed chromatogram results were obtained from injection of 3 ul of the extract showed peaks at retention time 5.53, 10.44 and 11.86 which represent phenylmorpholine, N-formyl loline, and N-acetyl loline, respectively. The values printed in the "amount" column represent the amount (ug) present in 0.5 ml of the extract (or from 25 mg of grass sample). This value is multiplied by 40 to obtain the amount in 1 gm of sample (ppm). Note that N-acetyl loline may only be present in trace amounts, ca 4 ppm.

Rosalin with an associated number is perennial ryegrass hosting the present endophyte *Neotyphodium siegelii* in accordance with present invention. Rosalin without a number or Rosalin (4n) is the non-infected host parent. The 237707 is the endophyte infected fescue donor.

| Run# 1417 | | Advanta | | |
|---|---|---|---|---|
| Workfile | | 50 mg 100 ml Na HCO₃ solution | | |
| Workfile Name: | | 1 ml PM | | |
| Sample # 1 | | | | |
| | ISTD RT | HEIGHT | TYPE | CAL # | AMOUNT |
|---|---|---|---|---|---|
| | 0.26 | 8388488 | tSPH | | 0.000 |
| | 0.44 | 2259335 | DTBP | | 0.000 |
| | 0.55 | 3270170 | DTPP | | 0.000 |
| | 0.66 | 2268258 | DTPB | | 0.000 |
| | 0.78 | 2882340 | DSHH | | 0.000 |
| | 0.90 | 2065830 | DSHH | | 0.000 |
| | 1.02 | 1577737 | DSHH | | 0.000 |
| | 1.15 | 1206964 | USHB | | 0.000 |
| | 3.16 | 4879 | TPV | 1 | 0.260 |
| | 3.54 | 8786 | TVV | | 0.000 |
| | 4.90 | 1322 | PP | | 0.000 |
| phenylmorpholine | 5.53 | 230566 | PB | 2& | 12.500 |
| | 7.40 | 1086 | BV | | 0.000 |
| | 8.64 | 3449 | PV | | 0.000 |
| | 9.07 | 2806 | VP | | 0.000 |
| N-Formyl Ioline | 10.44 | 144729 | PB | 3 | 24.973 × 40.0 = 999 ppm |
| N-Acetyl Ioline | 11.86 | 802 | BV | | 0.000 |
| | 12.98 | 1555 | VV | | 0.000 |
| | 15.05 | 2049 | PV | | 0.000 |
| | 16.83 | 24770 | VV | | 0.000 |
| | 17.39 | 5312 | VV | | 0.000 |
| | 17.78 | 6470 | VV | | 0.000 |
| | 18.39 | 4425 | VV | | 0.000 |
| | 22.91 | 47721 | VV | | 0.000 |
| | 30.35 | 25028 | VV | | 0.000 |
| | 34.05 | 46314 | VV | | 0.000 |

Total height = 2.4481E+07
ISTD AMT = 1.2500E+01
Sample AMT =

Example 3

Testing for Toxin Lolitrem B

A known alkaloid analysis as described was carried out to detect Lolitrem B.

The following process was employed:
Extraction and HPLC method for lolitrem B from plant material
Reagents
HPLC grade acetonitrile, methanol and chloroform were purchased from commercial sources.
Solutions
The extraction solution of chloroform/methanol (2/1 v/v) was prepared and stored indefinitely. The reconstitutions solution of chloroform/acetonitrile (4/1 v/v) was prepared and stored indefinitely.
Instruments
Equipment consisted of a binary HPLC pump (0.75 mL/min), an autosampler (50 µL injection volume), and a fluorescene detector with 7-µL flow cell ($\lambda$ex=268 nm, $\lambda$em=440 nm, response=2). Data collection was via a PC-based data system. A Hypercarb pH column (100×3.2 mm, 7 µm particle size) was used in conjunction with a guard column cartridge (10×4 mm) with similar packing.
Mobile phase
Mobile phase A consisted of chloroform/methanol (95/5) and mobile phase B consisted of acetonitrile/methanol (95/5). Each was made by measuring the methanol into a volumetric flask and diluting to volume with the appropiate solvent. The column was equilibrated with 40% A. After injection it ramped linearly to 80% A in 4 min., held for 4 min., ramped linearly to 100% A in 2 min., held for 6 min., and then returned to 40% A (linearly, over 3 min.) Time between injections was 23 min.
Sample Preparation
Dry plant material was ground in a sample mill to pas through 1-mm screen. Ground plant material (0.002 g) was weighted into a 12×75-mm polypropylene culture tube. To the tube was added 3 mL of the extraction solution. The tube was capped and rotated on a hematology chemistry mixer for 24 hr in the dark. The solids formed a sediment by centrifugation at 1700× g for 5 min and 1.8 mL of supernatant was transferred to a clean polypropylene culture tube. The solvent was evaporated under a flow of nitrogen at ambient temperature, and the residue was dissolved in 0.50 mL of the reconstitution solution. The extract was transferred to small-volume inserts in 12×32-mm autosampler vials.
Standards
A batch of seed, assayed by another laboratory to be 6,800 ppb lolitrem B by comparison with an authentic lolitrem B standard, was mixed with seed that gave no detectable lolitrem B by this method. This resulted in seed standards ranging from a minimum of 504 ppb lolitrem B to the maximum of 6,800 ppb. The standard set was used for sample runs and also to assay other batches of high-endophyte seed for use in preparing further sets of standards, and to assay batches of moderate-endophyte infected seed for use as a control. After establishing the value of the control batch of seed, it was run with every batch of samples.

Endophyte Toxin analysis Summary Report Lolitrem B

| Sample ID | Cultivars | Lolitrem B (ppb) |
|---|---|---|
| Seed | Rosalin | <100 |
| Seed | meadow fescue | <100 |
| Plant tissue | Rosalin 1 | <100 |
| Plant tissue | Rosalin 2 | <100 |
| Plant tissue | Rosalin 3 | 1494* |
| Plant tissue | Rosalin 4 | <100 |
| Plant tissue | Rosalin 5 | <100 |
| Plant tissue | Rosalin 6 | <100 |

*We have discussed that this may not actually be Lolitrem B.

This appears to be an artefact and not actually Lolitrem B. In one sample this appeared to be a contaminate. All other samples showed no significant evidence of this toxic alkaloid when the *Lolium perenne* L. was infected with *Neotyphodium siegelii*.

Example 4
Testing for Toxin Ergotamine
A known alkaloid analysis was carried out to detect Ergotamine and Lolitrem B.

Endophyte Toxin Analysis Summary Report Ergotamine

| Sample ID | Cultivars | Ergotamine Ergovaline (ppb) | Lolitrem B (ppb) |
|---|---|---|---|
| Seed | 237707 | <10 | <100 |
| Seed | Rosalin 4N | <10 | <100 |
| Seed | Aubisque 4N | <10 | <100 |
| Seed | Bastion 4N | <10 | <100 |
| Seed | Mongita 2N | <10 | <100 |
| Seed | Herbic 2N | <10 | <100 |
| Seed | Belramo 2N | <10 | <100 |

Final report
237707, Rosalin and Aubisque were checked for Ergotamine. None was found.
Aubisque had a peak eluting between Ergovaline and Ergotamine
The samples showed no significant evidence of this toxic alkaloid in the present invention.

Example 5
Testing for Toxin Ergovaline
An alkaloid analysis as known in the art was carried out to detect Ergovaline.
An example of this analysis is shown in J.Vet. Diagn. Invest. 6:348–352 (1994), the following table provides the results of this analysis. Improved extraction and HPLC methods for ergovaline from plant material and rumen fluid, A Morrie Craig, Ben Bilich, Jeanette T. Hovermale, Ronald E. Welty.

Endophyte Toxin Analysis Summary Report Ergovaline

| Sample ID | | Ergovaline (ppb) | Lolitrem B (ppb) |
|---|---|---|---|
| Rosalin 1 | Straw | <10 | <100 |
| Rosalin 2 | Straw | <10 | <100 |
| Rosalin 3 | Straw | <10 | <100 |
| Rosalin 4 | Straw | <10 | <100 |
| Rosalin 5 | Straw | <10 | <100 |
| Rosalin 6 | Straw | <10 | <100 |

Example 6

Example 1 was repeated and the endophyte was used to infect diploid forage cultivar Belramo (Diploid perennia), Tetrone (Tetraploid annual), Topspeed (Diploid annual) and Seine tall fescue. The above were all infected.

The results are as follows:

Tetrone (Tetraploid annual)=53 infected plants=25% infection rate Topspeed (Diploid annual)=6 infected plants=5.5% infection rate. Belramo (Diploid perennial)=12 infected plants=10% infection rate. The remaining cultivar (Seine tall fescue) was also infected.

The forest tall fescue (*Festuca arundinacea*) Seine had 224 seedlings inoculated with the novel endophyte. Of the 224 inoculations, 16 retained the novel endophyte. The 16 plants are maintained in the field and will produce seed in the summer of 2000.

The endophyte according to the present invention has been deposited under No. 74483 with the American Type Culture Collection (ATCC), located at 10801 University Boulevard, Manassas, Va. 20110-2209 on Jan. 22, 1999.

All publications, patents, and patent applications cited herein are considered to be indicative of the level of skill in the art, and are incorporated by reference.

We claim:

1. A selected grass infected with an endophyte, comprising: a selected grass host which is infected by a strain of *Neotyphodium siegelii* endophyte, a representative sample of said endophyte is on deposit at the ATCC with deposit number 74483, said endophyte having a native host of meadow fescue (*Festuca pratensis* grass and not having a native host of said selected grass.

2. A selected grass according to claim 1 wherein said selected grass is *Lolium perenne* L.

3. A selected grass according to claim 1 wherein said endophyte does not produce animal toxicoses.

4. A selected grass according to claim 1 wherein said endophyte increases the resistance of the selected grass to insect feeding.

5. A selected grass according to claim 1 wherein said endophyte does not produce herbivore toxic alkaloids.

6. Fodder or other animal feed made from the selected grass according to any one of claims 1 to 5.

7. Seed or other regenerative plant material from the selected grass according to any one of claims 1–5.

8. A method of employing the selected grass according to claim 1, comprising:

(a) selecting a parent grass of the same or a different variety than the selected grass,
   (b) forming progeny from the parent grass and the selected grass which has enhanced performance characteristics,
   (c) screening the progeny for said enhanced performance characteristics,
   (d) selecting the progeny with such characteristics, and
   (e) propagating the progeny.

9. A method of employing the selected grass according to claim 8 further comprising producing progeny seed from said progeny, and sowing the progeny seed wherein plant material carrying the endophyte is produced therefrom.

10. A method of employing the selected grass according to claim 8, further comprising harvesting the plant material produced by said progeny seed.

11. A method of employing the selected grass according to claim 8, further comprising selecting herbivores to graze on said plant material.

12. A method according to claim 8 wherein the parent grass is resistant to drought.

13. A method according to claim 8 wherein the parent grass is resistant to insect feeding.

14. A method according to claim 8 wherein the parent grass does not produce toxicoses in animals.

15. A *Lolium perenne* L. host infected with an endophyte, comprising: *Lolium perenne* L. which is hosting a strain of *Neotyphodium siegelii*, endophyte, a representative sample of said endophyte is on deposit at the ATCC with deposit number 74483, said endophyte producing enhanced performance characteristics in the host but said endophyte not producing herbivore toxic alkaloids in the host.

16. A *Lolium perenne* L. infected with *Neotyphodium siegelii* according to claim 15 wherein said endophyte is natively hosted by meadow fescue.

17. A *Lolium perenne* L. infected with an endophyte according to claim 15 wherein said endophyte is stably inherited in the progeny of said host by maternal transmission.

* * * * *

UNITED STATES PATENT AND TRADEMARK OFFICE
CERTIFICATE OF CORRECTION

PATENT NO. : 6,815,591 B1
DATED : November 9, 2004
INVENTOR(S) : K.W. Hignight et al.

It is certified that error appears in the above-identified patent and that said Letters Patent is hereby corrected as shown below:

Title page,
Item [73], Assignee, "Kapelie" should read -- Kapelle --.

Column 1,
Line 8, "No. ." should read -- No. --.
Line 20, "Endoophyte" should read -- Endophyte --.
Line 48, "Neothyphodium" should read -- *Neothyphodium* --.

Column 2,
Line 12, "(*Festucae*" should read -- (*Festuca* --.
Line 60, "Drechsiera" should read -- Drechslera --.
Line 61, "Rhizoctonia" should read -- *Rhizoctonia* --.

Column 3,
Line 13, "not, infected" should read -- not infected --.
Line 43, "20110" should read -- 20110, --.
Line 44, "74483" should read -- 74483, --.
Line 44, "1999" should read -- 1999. --.

Column 4,
Line 59, "3. Sterilise sheath" should read -- 3. Sterilise sheaths --.

Column 5,
Line 36, "end" should read -- and --.

Column 6,
Line 7, "(15 mmx0.53" should read -- 15 mx0.53 --.
Line 32, "Workfile" should read -- Workfile ID:C --.
Line 49, "Ioline" should read -- Loline --.
Line 50, "Ioline" should read -- Loline --.

Column 7,
Line 31, "pas" should read -- pass --.

UNITED STATES PATENT AND TRADEMARK OFFICE
CERTIFICATE OF CORRECTION

PATENT NO. : 6,815,591 B1
DATED : November 9, 2004
INVENTOR(S) : K.W. Hignight et al.

It is certified that error appears in the above-identified patent and that said Letters Patent is hereby corrected as shown below:

Column 8,
Lines 9-15, after "*We have discussed that this may not actually be Lolitrem B." the following should be keyed in 6 font size "This appears to be an artefact and not actually Lolitrem B. In one sample this appeared to be a contaminate. All other samples showed no significant evidence of this toxic alkaloid when the *Lolium perenne* L. was infected with *Neotyphodium siegelii.*"
Line 26, "*pratensis*" should read -- pratensis --.

Column 10,
Line 29, "*siegelii*, endophyte," should read -- *siegelii* endophyte --.

Signed and Sealed this

Twenty-ninth Day of November, 2005

JON W. DUDAS
*Director of the United States Patent and Trademark Office*